(12) United States Patent
Kukunas et al.

(10) Patent No.: US 11,576,756 B2
(45) Date of Patent: Feb. 14, 2023

(54) DENTAL ABUTMENT SCREW EXTRACTOR

(71) Applicant: University of Pittsburgh—Of the Commonwealth System of Higher Education, Pittsburgh, PA (US)

(72) Inventors: Steve J. Kukunas, Pittsburgh, PA (US); Ashley Smoots, Pittsburgh, PA (US); Hannah M. Smith, Pittsburgh, PA (US); Paul Kukunas, Pittsburgh, PA (US); Fanying Sun, Pittsburgh, PA (US); Tyler Hughes, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 474 days.

(21) Appl. No.: 16/690,926

(22) Filed: Nov. 21, 2019

(65) Prior Publication Data
US 2020/0100877 A1    Apr. 2, 2020

Related U.S. Application Data

(62) Division of application No. 15/500,467, filed as application No. PCT/US2015/044613 on Aug. 11, 2015, now Pat. No. 10,537,410.

(Continued)

(51) Int. Cl.
*A61C 8/00* (2006.01)
*A61B 17/92* (2006.01)
(Continued)

(52) U.S. Cl.
CPC ............ *A61C 8/0089* (2013.01); *A61B 17/92* (2013.01); *A61C 3/16* (2013.01); *A61C 8/00* (2013.01);
(Continued)

(58) Field of Classification Search
CPC ..... A61C 8/0089; A61C 8/0068; A61C 8/005; A61C 8/0048; A61C 3/16; A61B 17/92;
(Continued)

(56) References Cited

U.S. PATENT DOCUMENTS

| 4,265,618 A | * | 5/1981 | Herskovitz | ............. | A61C 5/50 |
| | | | | | 433/32 |
| 7,179,084 B1 | | 2/2007 | Kometas | | |

(Continued)

FOREIGN PATENT DOCUMENTS

| KR | 2003072093 A | * | 9/2003 |
| KR | 20030072093 | | 9/2003 |
| WO | WO 2005/104981 | | 11/2005 |

OTHER PUBLICATIONS

Choi et al., Device For Extracting Broken Bolt, Adhesive Storing Members Installed At Housing And Containing Adhesive And Drawing Member Of Drawing Adhesive From Adhesive Storing Member, (Year: 2003).*

(Continued)

*Primary Examiner* — Ralph A Lewis
*Assistant Examiner* — Mirayda A Aponte
(74) *Attorney, Agent, or Firm* — Klarquist Sparkman, LLP (57) ABSTRACT

Described herein are systems and methods for extracting a broken fragment of a dental abutment screw from a dental implant. One such system includes an extractor tool having a tubular outer body and a conductor positioned within the tubular outer body, and an applicator that receives and end of the extractor tool and also includes a heating element that converts electrical energy into heat that is conducted to the extractor tool to melt a thermoplastic adhesive in a cavity at the distal end of the extractor tool, such that the melted thermoplastic adhesive can conform to and engage with a broken fragment of a dental abutment screw within a dental (Continued)

implant when the adhesive cools. The extractor tool can then be rotated to unscrew the broken fragment from the dental implant.

15 Claims, 8 Drawing Sheets

Related U.S. Application Data

(60) Provisional application No. 62/036,491, filed on Aug. 12, 2014.

(51) Int. Cl.
*A61F 7/00* (2006.01)
*A61C 3/16* (2006.01)
*A61B 17/00* (2006.01)

(52) U.S. Cl.
CPC ............ *A61C 8/0068* (2013.01); *A61F 7/007* (2013.01); *A61B 2017/00955* (2013.01); *A61F 2007/0013* (2013.01)

(58) Field of Classification Search
CPC ......... A61B 17/88; A61B 17/58; A61B 17/56; A61B 2017/00955; A61B 2017/00831; A61F 7/007; B61F 2007/0013; B61F 2007/0002; B61F 2007/0001
USPC ............................ 433/32; 173/13; 285/120.1
See application file for complete search history.

(56) References Cited

U.S. PATENT DOCUMENTS

| | | |
|---|---|---|
| 2007/0123909 A1 | 5/2007 | Rupp et al. |
| 2010/0304335 A1 | 12/2010 | Garcia Saban et al. |
| 2014/0113245 A1 | 4/2014 | Heo et al. |
| 2015/0216638 A1* | 8/2015 | Baaske ............... A61C 13/1016 433/199.1 |
| 2017/0209242 A1 | 7/2017 | Kukunas et al. |

OTHER PUBLICATIONS

Ebnesajjad et al., "Hot Melt Adhesives," https://www.sciencedirect/com/topics/materials-science/hot-melt-adhesives, downloaded Nov. 22, 2018, 9 pages.

International Search Report and Written Opinion for related International Application No. PCT/US2015/044613, dated Nov. 13, 2015, 11 pages.

* cited by examiner

DENTAL ABUTMENT SCREW EXTRACTOR

CROSS-REFERENCE TO RELATED APPLICATIONS

This application is a divisional of U.S. patent application Ser. No. 15/500,467 filed Jan. 30, 2017, which is the U.S. National Stage of International Application No. PCT/US2015/044613 filed Aug. 11, 2015, which claims the benefit of U.S. Provisional Application No. 62/036,491 filed Aug. 12, 2014, all of which are incorporated by reference herein in their entirety.

FIELD

This application is related systems, devices and methods for removing a broken dental abutment screw from a dental implant.

BACKGROUND

Figure 1:
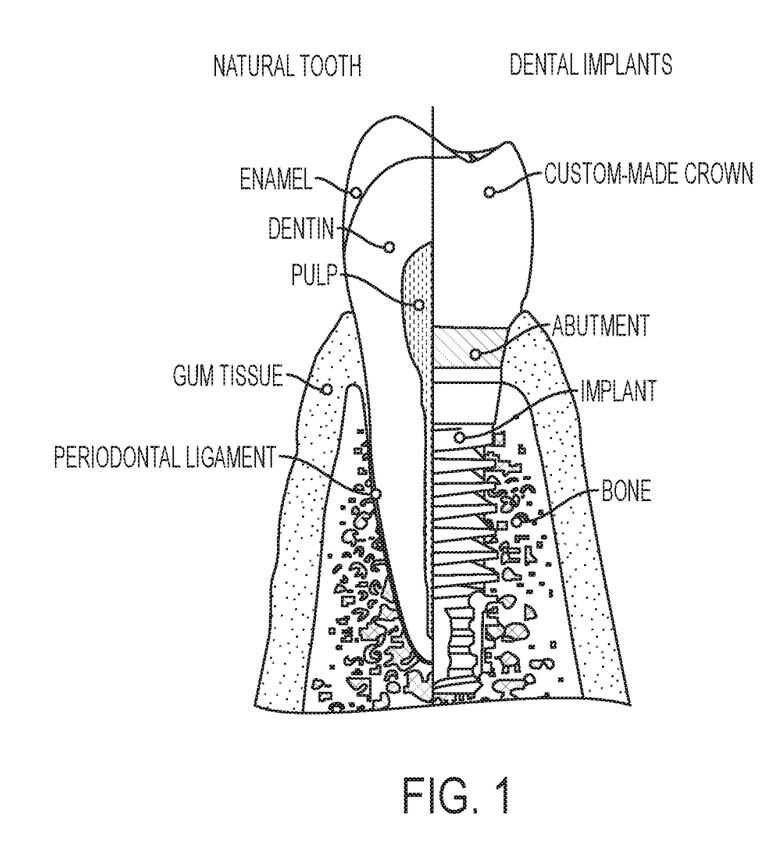
FIG. 1 is a schematic diagram of an exemplary dental prosthesis implanted in a patient, in comparison to a natural tooth.
Figure 2:
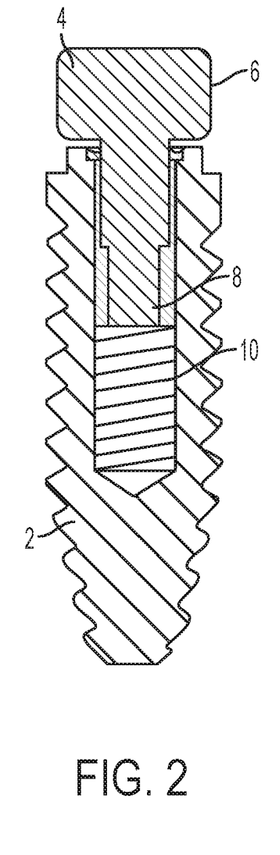
FIG. 2 is a side view, partially in cross-section, of an exemplary dental implant and abutment screw of a dental prosthesis.

FIG. 1 shows a conventional dental prosthesis for replacing a natural tooth. The dental prosthesis includes a dental implant that is implanted into a patient's bone. A dental abutment and screw are mounted on the dental implant. The abutment screw is torqued to approximately 35 N-cm. A crown can then be mounted on the abutment screw. FIG. 2 shows an exemplary dental implant 2 with an exemplary abutment screw 4 mounted in the implant. The screw 4 includes an abutment head 6, a neck 8, and a threaded portion 10 that is engaged with inner threads of the implant 2. Sometimes such an abutment screw can break at the neck 8 such that the abutment screw head 6 is removed but the threaded portion 10 and perhaps some of the neck remains stuck in the dental implant. This can happen, for example, due to excessive torque off axis or excessive forces on the mouth. Removing a remnant of a broken abutment screw from within a dental implant can be clinically challenging.

One removal technique is to drill a small hole within the broken fragment with reverse-oriented threads, then insert a smaller screw or tool into the reverse threads to unscrew the broken screw fragment. Another approach is to create a groove in the broken screw fragment to assist is turning it with a tool similar to a screw driver.

However, these approaches can be problematic because they can further damage the broken screw fragment, can damage the internal dental implant threads, can cause the broken screw fragment to break up into smaller pieces, and/or can damage the surrounding dental implant. Another approach sometimes used is to manually attempt to turn the screw fragment with a dental explorer, however this technique can be time consuming and difficult to accomplish. Another approach is to use an ultrasonic instrument to pulsate the screw fragment and encourage rotational force.

SUMMARY

Described herein are systems, devices, and methods for extracting a broken fragment of a dental abutment screw from a dental implant.

An exemplary disclosed method for extracting a broken fragment of a dental abutment screw from a dental implant comprises positioning an extraction tool in a patient's mouth such that a thermoplastic adhesive in a distal end portion of the extraction tool is adjacent to a broken fragment of a dental abutment screw that is mounted within a dental implant in the patient's mouth; applying heat to the thermoplastic adhesive via the extraction tool to melt the thermoplastic adhesive such that the thermoplastic adhesive conforms to surfaces of the broken fragment; allowing the thermoplastic adhesive to cool such that it solidifies and bonds the extraction tool to the broken fragment; and rotating the extraction tool to unscrew the broken fragment from the dental implant.

An exemplary disclosed system comprises an extractor tool having a tubular outer body and a conductor positioned within the tubular outer body. The extractor tool can have a bent "L" shape, a straight "I" shape, or other shapes. The system can also include an applicator device that provides heat to the extractor tool. In some embodiments, a handheld applicator device includes a collet that receives and holds a proximal end of the extractor tool and also includes a heating element that converts electrical energy into heat that is conducted along the conductor to melt a thermoplastic adhesive in a cavity at the distal end of the extractor tool such that the melted thermoplastic adhesive can bond the extractor tool to a broken fragment of a dental abutment screw within a dental implant when the adhesive cools. In other embodiments, a bench top applicator device includes a heating element that temporarily receives the distal end of the extractor tool and applies heat to the distal end of the extractor tool, then the extractor tool is removed from the heating element and applied to a broken abutment screw. In such embodiments, a proximal end of the extractor tool can include an insulated gripping portion for a user to hold and manipulate the extractor tool. The extractor tool can then be rotated to unscrew the broken fragment from the dental implant.

The foregoing and other objects, features, and advantages of the disclosed technology will become more apparent from the following detailed description, which proceeds with reference to the accompanying figures.

DETAILED DESCRIPTION

Described herein are systems, devices, and methods for removing a broken dental abutment screw from a dental implant using a thermoplastic adhesive to attach an extraction tool to the broken screw such that the extraction tool can be rotated to unscrew the broken screw from the dental implant.

Figure 3:
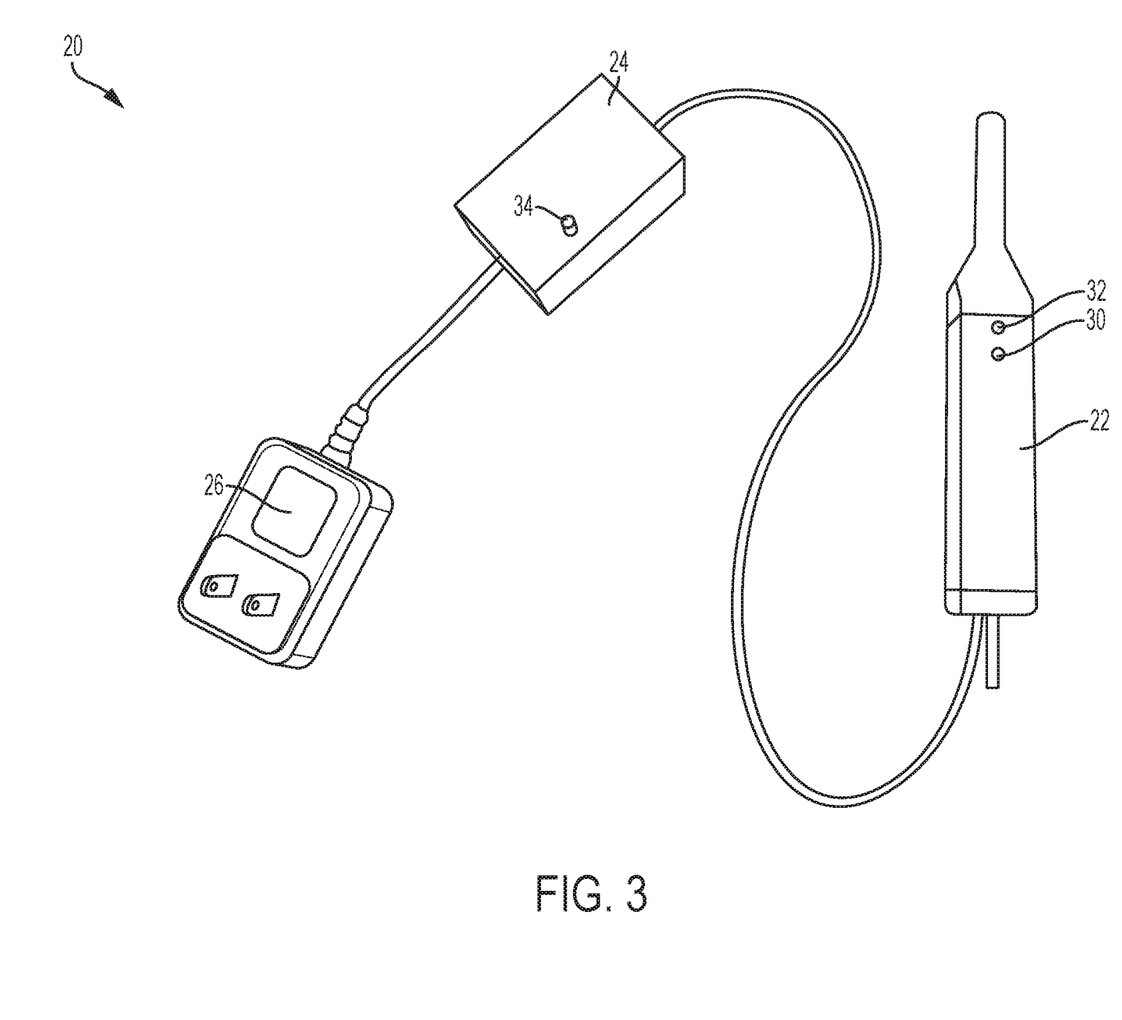
FIG. 3 shows an exemplary system for extracting a broken abutment screw.
Figure 5:
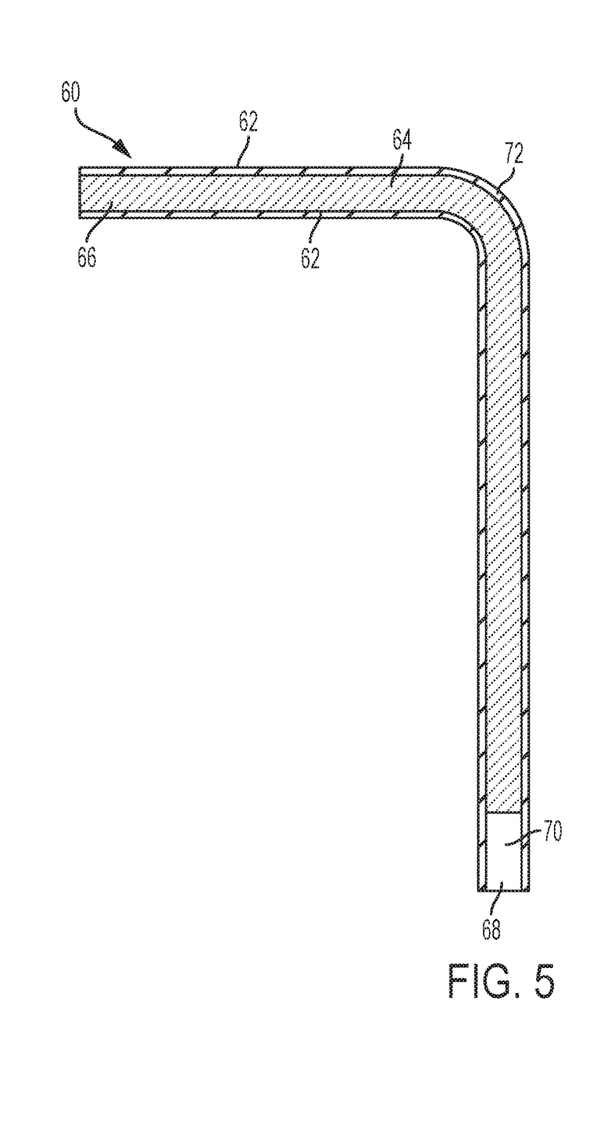
FIG. 5 is a cross-sectional view of an exemplary extraction tool used with the system of FIG. 3.
Figure 9:
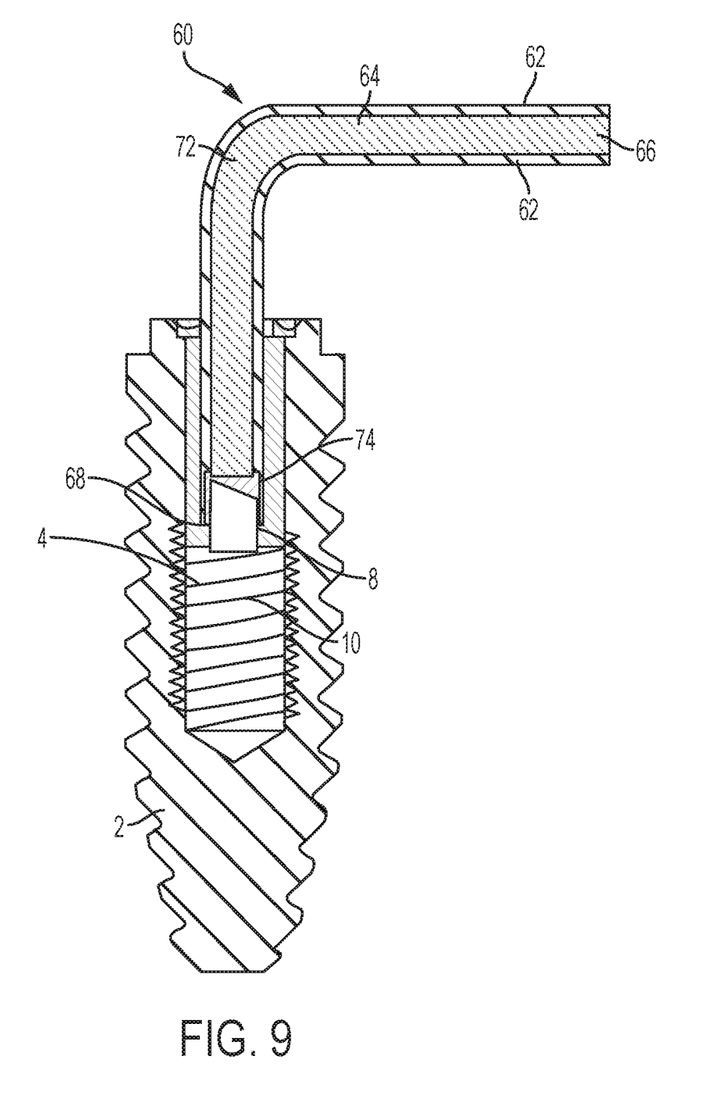
FIG. 9 is a side cross-sectional view of the extraction tool of FIG. 5 secured to a broken fragment of an abutment screw within a dental implant.

FIG. 3 shows an exemplary system 20 for removing a broken dental abutment screw using a screw-specific extraction tool, such as the tool 60 illustrated in FIG. 5, along with a thermoplastic adhesive. FIG. 9 shows the tool 60 of FIG. 5 having been secured to a broken neck portion 8 of an abutment screw 4 with a thermoplastic adhesive 74 using the system of FIG. 3.

The system 20 shown in FIG. 3 includes an applicator 22, a controller 24, and a plug 26, which are electrically coupled together via wires. In alternative embodiments, the components of the controller 24 can be combined with the plug 26 to simplify the system 20.

The plug 26 attaches to a power source, such as a common AC power outlet, and is configured to convert electrical power from AC to DC at a specified voltage for use by the controller 24 and applicator 22.

Figure 7:
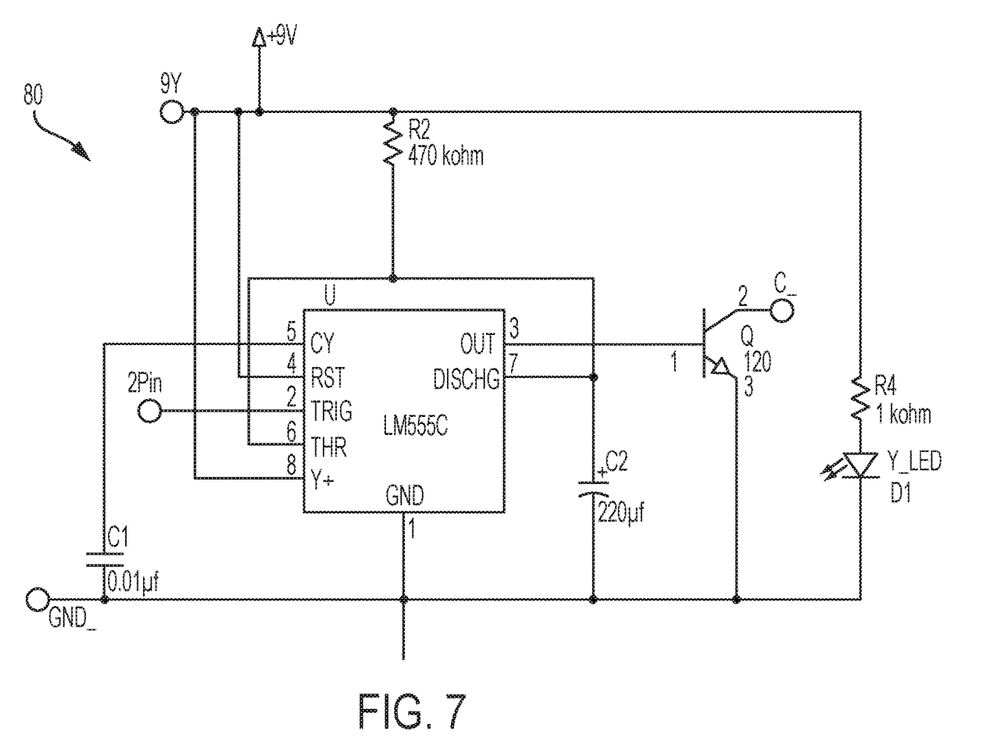
FIG. 7 shows an exemplary electrical circuit for the system of FIG. 3.

The controller 24 can include electrical circuitry that controls the power supplied from the plug 26 to the applicator 22 for generating heat. The controller 24 can include a time-controlled circuit, for example, that applies a predetermined level of power to the applicator 22 over a predetermined period of time after it is activated. The predetermined level of power and the predetermined period of time can be selected based on the type of thermoplastic adhesive that is used and/or other application-specific factors. The controller 24 can include a light or other indicator 34 that indicates when the plug 26 is coupled to a power source and the controller is available for supplying power to the applicator 22. An exemplary electrical circuit diagram 80 for the controller 24 is shown in FIG. 7. The exemplary circuit 80 utilizes a 555 timer that acts as a clock. The amount of time that passes is based upon the capacitors and resistors placed in series. The 555 timer is in monostable configuration, meaning that only one pulse is produced with each triggered operation.

Figure 4:
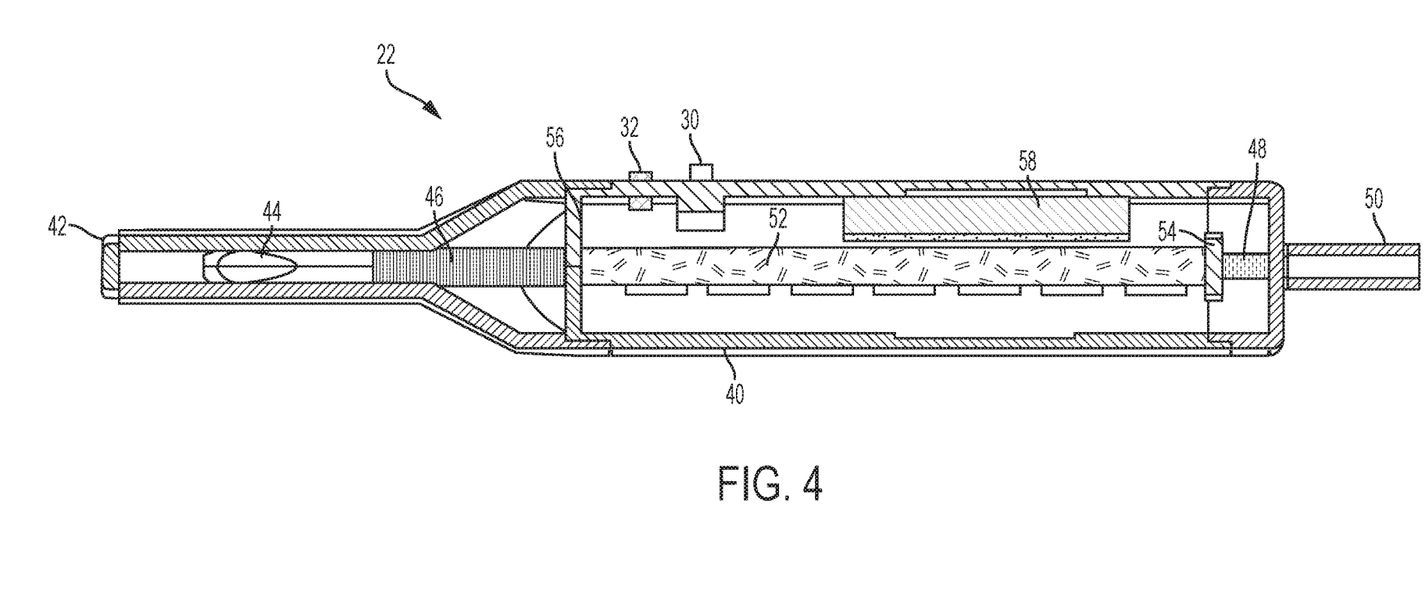
FIG. 4 is a longitudinal cross-sectional view of an exemplary hand-held applicator of the system of FIG. 3.

The applicator 22 is shown in longitudinal cross-section in FIG. 4. The applicator 22 includes a body or frame or housing 40 that is shaped to be held by a user in one hand and has a distal end 42 having a relatively narrow dimension for inserting into a patient's mouth. The applicator 22 also includes a collet 44 located near the distal end 42 that is configured to receive and retain a tool, such as the tool 60 shown in FIG. 5, for engaging a broken dental abutment screw in a patient's mouth. A heating element, or filament, 46 is positioned adjacent to the collet 44 and is configured to be thermally coupled to the tool when it is inserted into the collet. The heating element 46 may be in direct contact with the tool or there can be an intermediate conductive material, such as a portion of the collet 44, therebetween. The heating element 46 converts electricity to heat that is conducted along the extraction tool to a thermoplastic adhesive located at the distal end of the tool in order to melt the adhesive and secure the tool to a broken abutment screw.

Figure 8:
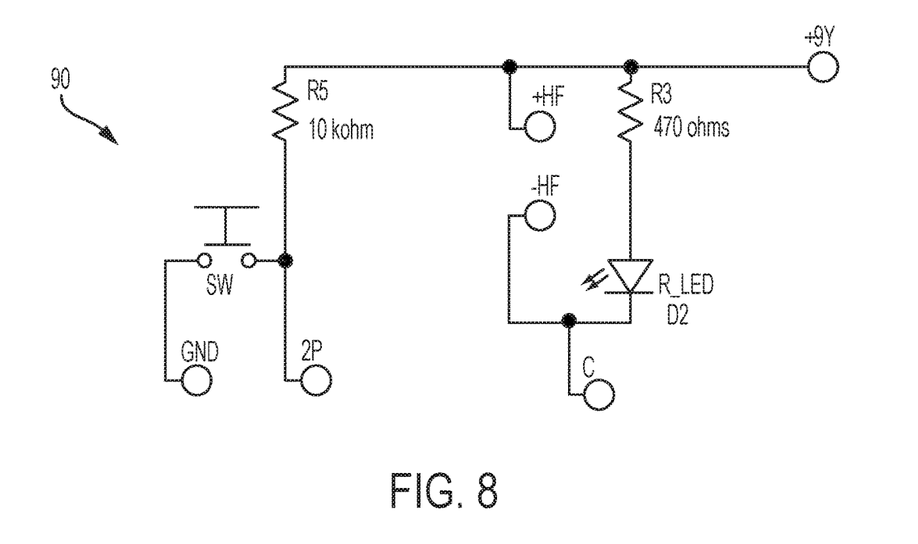
FIG. 8 shows another exemplary electrical circuit for the system of FIG. 3.

The heating element 46 is electrically coupled to the controller 24 and to a circuit 58 located within the applicator 22. An exemplary circuit diagram 90 for the circuit 58 is shown in FIG. 8. In some embodiments, the circuit 58 can be combined with the circuitry in the controller 24 to minimize the bulkiness of the applicator 22. At least one activator, button, or other control 30 is provided on the applicator 22 that the user can press or otherwise interact with to cause circuit 58 and/or the controller 24 to begin supplying power to the heating element 46. A light or other indicator 32 can also be provided on the applicator 22 to indicate when the heating element 46 is actively powered. Although not shown in FIG. 4, wiring can be included in the applicator 22 to electrically coupled the heating element 46, the circuit 58, the activator 30, and the light 32, and/or other electrical components in the applicator, and to electrically couple the applicator to the controller 24.

As further shown in FIG. 4, the applicator 22 can include a mechanism for inserting, securing, and releasing a selected extraction tool. FIG. 4 shows one exemplary mechanism wherein a shaft 48 extends longitudinally through the applicator 22 with a distal end of the shaft coupled to the collet 44 and a proximal end of the shaft coupled to a plunger 50 that extends from the proximal end of the body 40. A spring 52 can be positioned around or alongside the shaft 48 to bias the shaft, plunger 50, and collet 44 toward a proximal position that is shown in FIG. 4. A distal end of the spring 52 can abut a wall 56 that is fixed relative to the body 40 and a proximal end of the spring can abut a washer 54 that is fixed relative to the shaft 48. As the user presses the plunger 50 distally into the body 40, the shaft and washer 54 move distally and compress the spring 52 between the washer 54 and the wall 56. The distal motion of the shaft 48 also causes the collet 44 to move distally such that the collet moves partially out of the distal end 42 of the body. This allows the collet 44 to radially expand such that the collet can receive a proximal end of a selected extraction tool, such as the proximal end 66 of the tool 60 shown in FIG. 5. Once the tool is inserted into the collet 44, the plunger 50 can be released by the user, such that the compressed spring 52 pushes the washer 54 and shaft 48 back proximally toward the proximal position shown in FIG. 4. This proximal motion of the shaft 48 pulls the collet 44 and inserted tool into the distal end 42 of the body, wherein the collet becomes radially compressed and grips the tool securely. When the collet is retracted into the body 40, the distal end of the tool and/or the collet 44 can be in contact with the heating element 46 such that heat can be conducted from the heating element, through the tool to the thermoplastic adhesive at the distal end of the tool.

In other embodiments, the applicator 22 can include other mechanisms for inserting, securing, and/or releasing a selected extraction tool. For example, the applicator 22 can include a push mechanism at the distal end 42 of the body that can be pushed by a user to release or detach a tool. Another alternative is to use a more ergonomic lever and spring mechanism. By pressing on the lever, the spring is compressed to expose the collet.

Figure 6:
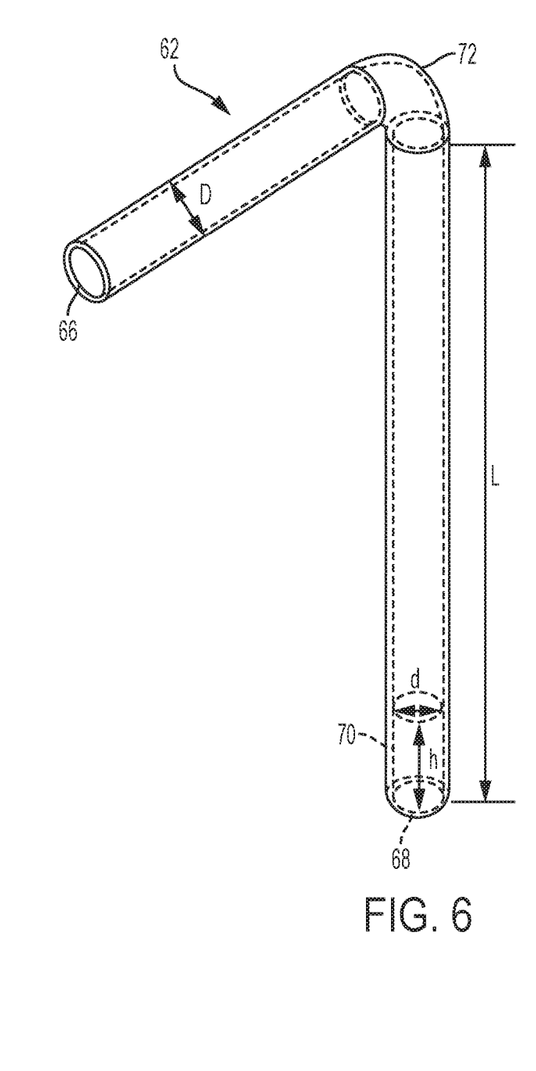
FIG. 6 is a perspective view of the exemplary extraction tool of FIG. 5.

FIG. 5 is a cross-sectional view of an exemplary extraction tool 60 that can be secured to a broken dental abutment screw (as shown in FIG. 9) and torqued to unscrew the broken dental abutment screw from a dental implant. The tool 60 comprises a tubular body 62 and an inner conductor 64 that are bent at an elbow 72 or otherwise formed in a non-straight shape, such as at a substantially perpendicular shape. The body 62 is shown in more detail in FIG. 6. The tool 60 has a proximal end 66 that is configured to be inserted into and secured by the collet 44 of the applicator 22, and has a distal end 68 that is configured to be secured to a broken dental abutment screw. The conductor 64 is positioned with the body 62 and extends from the proximal end 66 of the tool to a location short of the distal end 68 of the tool, forming a cavity 70 within the distal end of the body 62. The cavity 70 can be loaded with a thermoplastic adhesive in a solid state. The dimensions "h" and "d" of the cavity 70 (see FIG. 6) can be selected based on the size and shape of the broken dental abutment screw and the dental implant, the particular type of thermoplastic adhesive being used, and/or other factors. Similarly, the dimensions "L" and "D" of the body 62 can be selected based on the size and shape of the broken dental abutment screw and the dental implant, the position of the dental implant in the patient's mouth, the size and shape of the patient's mouth, the size and shape of the applicator and the collet, and/or other factors.

In some embodiments, the distal end of the body 62 of the tool can be tapered or the tool can further include a tapered annular body that fits around the distal end of body 62. Such a tapered outer surface at the distal end of the tool can also the tool to conform to certain dental implants that include a tapered opening into which the abutment screw is inserted. In some embodiments, the tapered outer surface of the tool can more fully fill the abutment screw opening in the dental implant when the tool is in contact with the broken screw fragment inside the implant. This can ensure an accurate alignment of the tool with the broken screw, and can reduce movement of the tool relative to the screw fragment while the thermoplastic adhesive solidifies to provide a stronger bond.

The body 62 can comprise any sufficiently rigid material and has a relatively low thermal conductivity relative to the conductor 64 (e.g., stainless steel or titanium), such that the body 62 can act to transmit sufficient torque for unscrewing the broken screw and can act as an insulator around the conductor as heat flows from through the conductor to the adhesive. The conductor 64 can comprise copper or other material having a high thermal conductivity.

The thermoplastic adhesive can be selected such that is provides sufficient adhesive strength when bonding to the broken abutment screw (e.g., titanium alloy) and the tool (e.g., stainless steel, copper, etc.). Desirable adhesives feature a low melting point (e.g., under 100° C.) and nontoxic substrates. Exemplary thermoplastic adhesives include ethylene-vinyl acetate and ethylene-acrylate. Dental sticky wax can also be used as the adhesive. Dental sticky wax can include various materials that typically include natural beeswax or synthetic beeswax and a resin. Exemplary sticky waxes include Trubyte® Waxes available from Dentsply and fall under Federal Specification number U-W-00149a. The thermoplastic adhesive can have a melting temperature that is sufficiently above room temperature so that it remains solid until heat is applied during use, but not too high so that it is safe for use within a patient's mouth and so that it can be melted quickly without too much heat needing to be applied from the system 20. For example, the melting temperature of the thermoplastic adhesive can be between about 50° C. and about 100° C., such as about 80° C.

Prior to use, the thermoplastic adhesive can be placed in the cavity 70 at the distal end of the tool 60 such that the thermoplastic adhesive is in contact with the conductor 64 and completely or partially fills the cavity 70.

The system 20 can be used with a variety of differently configured tools to remove different types and sizes of screws from different tooth locations and different sized mouths. The system 20 can be provided with a set of differently configured tools to choose from to extract a give broken dental abutment screw. For example, the user can match the inner diameter "d" and depth "h" of the cavity 70 (FIG. 6) to the diameter and height of the broken neck 8 (see FIG. 2) of the dental abutment screw 4 to the inner diameter. The user can also match the length "L" of the tool 60 to fit the tool comfortably within the patient's mouth.

The selected tool 60 with a thermoplastic adhesive 74 loaded in the cavity 70 can then be loaded into the collet 44 of the applicator 22 and the plug 26 can be connected to a power source to provide power. As illustrated in FIG. 9, the distal end 68 of the tool 60 can then be placed into the dental implant 2 such that the thermoplastic adhesive 74 contacts the top of the screw fragment within the dental implant. The outer diameter at the distal end 68 of the tool 60 can be sized small enough to fit into the opening of the dental implant 2 to access the broken fragment of the abutment screw 4.

The user can then press the activator 30 on the applicator 22 to being heat application from the heating element 46 through the conductor 64 to the thermoplastic adhesive 74 while holding the thermoplastic adhesive against the top of the broken screw 4. As the thermoplastic adhesive 74 melts, it can conform around the exposed upper end of the broken screw 4 (e.g., the neck portion 8) and the distal end 68 of the body 62 can lower around the sides of the upper end of the broken screw, as illustrated in FIG. 9. A dental abutment screw typically fractures at the narrow neck region 8, which is narrower than the surrounding inner walls of the implant 2, leaving an annular gap between the fractured neck 8 and the inner walls of the implant 2. The distal end 68 of the body 62 can move down into this annular gap, as shown in FIG. 9, as the thermoplastic adhesive 74 melts and the broken neck 8 moves into the cavity 70.

The melting process can take about two minutes, in one embodiment, and can take longer or shorter times in other embodiments. The circuit 80 in the controller 24 can be set to supply power to the heating element for a predetermined time, such as two minutes, then turn the heating element off. When the melting process is complete, the light 32 can turn off to signal the user.

Once the heating element 44 is turned off and the thermoplastic adhesive 74 is melted, the applicator 22 and tool 60 can continue to be held stationary relative to the screw fragment 4 while the thermoplastic adhesive 74 solidifies and bonds to the screw fragment and the tool. The small diameter of the distal end of the extraction tool minimizes the risk of interference with the dental implant. The cooling process can optionally be assisted by applying cool air flow over the tool 60. This can be performed, for example, by using conventional dental air tool to blow air over the tool 60. This can take about 15 seconds, in one example. Other fluids, such as other gasses or water, can also be used to cool the tool. Cooling the tool cause heat to be conducted away from the thermoplastic adhesive 74 through the tool 60.

Once the tool 60 is adhered to the broken screw via the solidified thermoplastic adhesive 74 (as shown in FIG. 9), the tool can be ejected or disengaged from the collet 44 of the applicator 22 by depressing the plunger 50. The tool 60 can then be manually rotated, similar to an Allen wrench, to unscrew the broken screw 4 from the dental implant 2. The elbow 72 in the tool 60 can help the user apply a sufficient torque using the proximal end 66 as a lever arm to rotate the tool.

In other embodiments, the disclosed extraction tool 60 can be used with other heat sources to supply the needed heat to melt the adhesive. In other embodiments, the extraction tool 60 can include a heating element, such as within the body 62 and contacting the conductor 64, which can be electrically coupled to an external power source.

Figure 10:
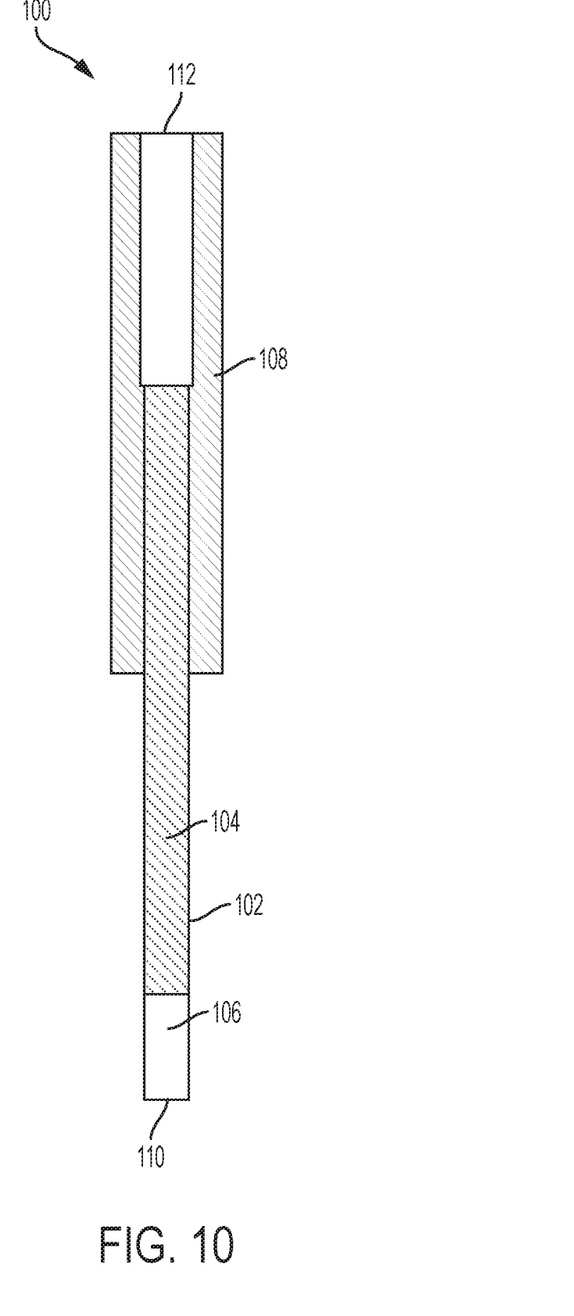
FIG. 10 is a side cross-sectional view of another exemplary extraction tool.
Figure 11:
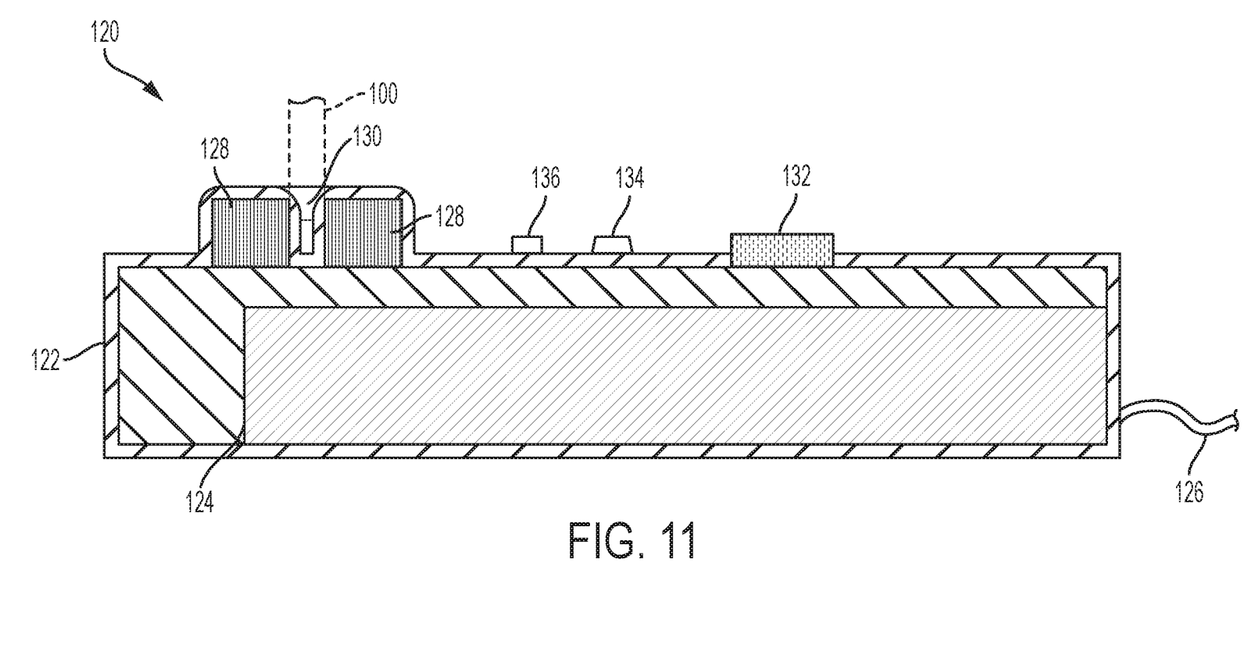
FIG. 11 is a side cross-sectional view of an exemplary bench top applicator device for applying heat to the extraction tool of FIG. 10.

In some embodiment, a bench top applicator can be used to supply heat to an extractor tool, and then the heated extractor tool can be disconnected from the applicator and manually applied to a broken abutment screw in the mouth. For example, FIGS. 10 and 11 illustrate an extractor tool 100 and a bench top applicator device 120. The extractor tool 100 can have be straight (as shown in FIG. 10) or have a bent "L" shape or other bent shape. The tool 100 includes a tubular body 102 (e.g., stainless steel) with another material, such as a conductor metal (e.g., copper) 104 inside the tubular body 102. The conductor 104 can stop short of a distal end 110 of the tubular body 102 to provide a cavity 106 for the thermoplastic adhesive. The proximal end 112 of the extractor 100 can include a grip 108 that acts as an insulator for a user to hold and manipulate the extractor. For example, the grip 108 can comprise silicone or other insulating material that also provides enough grip to allow the user to apply forces to the extractor. The grip 108 can extend over and cover the proximal end of the body 102 and conductor 104 for safety and to minimize heat loss through the proximal end.

The applicator 120 shown in FIG. 11 includes a rigid body 122, electrical circuitry 124 inside the body, a power supply cord 126 or other power source, an electrical heating element 128 with a central recess 130, an activator 132, and optionally indicators 134 and 136. The applicator 120 is configured to remain stationary while the extractor 100 is applied to the applicator for heating and then removed from the applicator to manually introduce the extractor into the mouth. The distal end 110 of the extractor 100 is inserted into the recess 130 in the heating element 128 and the activator is used to start the heating process. Electrical power is converted to heat by the heating element 128, and the heat is conducted into the extractor 100. The distal end 110 of the extractor can be inserted to a depth sufficient to heat the adhesive in the pocket 106 and heat the conductor 104. The indicator 134 can illuminate when the power cord 126 is plugged in and the device has power, and the indicator 136 can illuminate when the activator 132 is activated until a predetermined time has elapsed, after which the indicator turns off to indicate to the user that the heating process is complete and the extractor 100 can be removed from the heating element 128 and applied to a broken abutment screw. Circuitry similar to that shown in FIGS. 6 and 7 can be included in the circuitry 124 of the applicator 120.

After the extractor 100 is heated and removed from the applicator 120, the user can hold the extractor by the insulated grip 108 and apply the cavity 106 over a broken abutment screw. The conductor 104 retain heat and can help maintain the thermoplastic adhesive at a sufficiently high temperature during the transfer until it is engaged with the broken screw. The user can hold the extractor 100 with sufficient pressure on the broken screw until the thermoplastic adhesive cools and sets around the broken screw to create a sufficiently strong bond or fit with the broken screw. The user can then rotate the extractor 100 by twisting the grip 108 with his fingers or with another tool, such as forceps or the like, to remove the broken screw.

The technology disclosed herein with regard to removing a broken dental abutment screw can also be used for removing other types of broken screws, such as other types of dental screws or similar screws used in other parts of the body.

Any of the features or technologies described herein in relation to any one or more of the described embodiments can also be used with or included in any of the other described embodiments where possible, even if such features or technologies are not specifically mentioned in direct connection to a specific embodiment.

The singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A and/or B" means "A", "B" or "A and B."

Although methods and materials similar or equivalent to those described herein can be used in the practice or testing of the present technology, only certain suitable methods and materials are described herein. In case of conflict, the present specification, including terms, will control. In addition, the materials, methods, and devices are illustrative only and not intended to be limiting.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A system for extracting a broken fragment of a dental abutment screw from a dental implant in a patient's mouth, the system comprising:
    an extractor tool comprising a tubular outer body, a conductor positioned within the tubular outer body, and a cavity at a distal end of the extractor tool; and
    an applicator having a receiver that receives a proximal end of the extractor tool, the applicator also having a heating element that converts electrical energy into heat;
    wherein the extractor tool is configured to contain a thermoplastic adhesive in the cavity at the distal end of the extractor tool and the applicator is configured to conduct heat from the heating element to the extractor tool and to the thermoplastic adhesive to melt the thermoplastic adhesive such that the thermoplastic adhesive can conform to and engage with the broken fragment of the dental abutment screw within the dental implant.

2. The system of claim 1, wherein the conductor located within the tubular outer body has a proximal end and a distal end, wherein the distal end of the conductor forms a proximal end of the cavity and the distal end of the tubular outer body forms a distal end of the cavity, such that thermoplastic adhesive positioned in the cavity is in contact with the conductor.

3. The system of claim 1, further comprising a time-controlled circuit configured to provide a predetermined level of electrical power to the heating element for a predetermined period of time upon activation by a user.

4. The system of claim 1, wherein the extractor tool includes an insulating grip positioned around the proximal end of the tubular outer body.

5. The system of claim 1, wherein the extractor tool includes an elbow or bend along its longitudinal length.

6. The system of claim 1, wherein the applicator comprises:
    a rigid body shaped and sized to be hand-held by a user, the rigid body having a distal end and a proximal end and a longitudinal axis extending between the distal and proximal ends;
    a collet positioned in the rigid body near the distal end and configured to receive and release the proximal end of the extractor tool;
    the heating element being positioned in the rigid body adjacent to the collet, the heating element being coupleable to an electric power source and operable to convert electrical power into heat; and an activator electrically coupled to heating element and configured to cause electrical power to be supplied to the heating element upon activation by athe user;

wherein the applicator is operable to conduct heat generated by the heating element to the extractor tool held in the collet such that the heat causes the distal end of the extractor tool to become adhesively secured to the broken fragment of the dental abutment screw in the dental implant in the patient's mouth.

7. The system of claim 6, the applicator further comprising:
- a shaft fixed to the collet and extending from the collet through the rigid body along the longitudinal axis;
- a plunger fixed to a proximal end of the shaft; and
- a spring mounted around the shaft between the plunger and the collet;
- wherein a distal end of the spring is fixed relative to the rigid body of the applicator and a proximal end of the spring is fixed relative to the shaft, such that depressing the plunger distally relative to the rigid body moves the shaft and collet distally relative to the rigid body and compresses the spring, and such that releasing the plunger allows the spring to resiliently expand to move the shaft and collet proximally relative to the rigid body.

8. The system of claim 7, wherein moving the collet distally causes the collet to expand radially to receive or release the extractor tool, and moving the collet proximally causes the collet to contract radially to secure the extractor tool in the applicator.

9. The system of claim 6, the applicator further comprising an indicator light and an electrical circuit mounted in the body, the electrical circuit configured to illuminate the indicator light when electrical power is being supplied to the heating element in response to the user activating the activator.

10. The system of claim 6, the applicator further comprising a control circuit located remote from the rigid body and electrically coupled to the heating element and the activator.

11. A system for extracting a broken fragment of a dental abutment screw from a dental implant in a patient's mouth, the system comprising:
- an extractor tool comprising a tubular outer body, a conductor positioned within the tubular outer body, and a cavity at a distal end of the extractor tool; and
- an applicator having a receiver that receives a proximal end of the extractor tool, the applicator also having a heating element that converts electrical energy into heat;
- wherein the extractor tool is configured to contain a thermoplastic adhesive in the cavity at the distal end of the extractor tool and the applicator is configured to conduct heat from the heating element to the extractor tool and to the thermoplastic adhesive to melt the thermoplastic adhesive such that the thermoplastic adhesive can conform to and engage with the broken fragment of the dental abutment screw within the dental implant; and
- wherein the applicator further comprises a spring-biased plunger coupled to a collet, wherein depressing the spring-biased plunger causes the collet to open for receiving or releasing the extractor tool, and wherein releasing the spring-biased plunger causes the collet to close to secure the extractor tool to the applicator.

12. The system of claim 11, wherein the conductor located within the tubular outer body has a proximal end and a distal end, wherein the distal end of the conductor forms a proximal end of the cavity and the distal end of the tubular outer body forms a distal end of the cavity, such that thermoplastic adhesive positioned in the cavity is in contact with the conductor.

13. The system of claim 11, further comprising a time-controlled circuit configured to provide a predetermined level of electrical power to the heating element for a predetermined period of time upon activation by a user.

14. The system of claim 11, wherein the extractor tool includes an insulating grip positioned around the proximal end of the tubular outer body.

15. The system of claim 11, wherein the extractor tool includes an elbow or bend along its longitudinal length.

\* \* \* \* \*